United States Patent [19]

Livingston

[11] Patent Number: 5,025,037

[45] Date of Patent: Jun. 18, 1991

[54] USES FOR THE ORAL USE OF OAK POISON PREVENTATIVE IN THE TREATMENT OF: FELINE LEUKEMIA, INCREASED WOOL PRODUCTION IN SHEEP, AND REDUCTION OF SHIPPING FEVER IN STRESSED ANIMALS

[76] Inventor: William H. Livingston, 3003 N. 13th St., Artesia, N. Mex. 88210

[21] Appl. No.: 434,781

[22] Filed: Nov. 3, 1989

[51] Int. Cl.$^5$ ..................... A61K 31/19; A61K 33/26
[52] U.S. Cl. .................................. 514/574; 424/646; 424/648
[58] Field of Search ................. 424/648, 646; 514/574

[56] References Cited

U.S. PATENT DOCUMENTS

| | | | |
|---|---|---|---|
| 2,816,854 | 12/1957 | Gross | 424/697 |
| 4,041,153 | 8/1977 | Howard | 424/653 |
| 4,362,710 | 12/1982 | Watanabe | 424/422 |

*Primary Examiner*—Glennon H. Hollrah
*Assistant Examiner*—Gary E. Hollinden

[57] ABSTRACT

New uses for the Oak Poison Preventive supplement, including the treatment of feline leukemia, shipping fever in cattle, and increased wool production in sheep.

3 Claims, No Drawings

USES FOR THE ORAL USE OF OAK POISON PREVENTATIVE IN THE TREATMENT OF: FELINE LEUKEMIA, INCREASED WOOL PRODUCTION IN SHEEP, AND REDUCTION OF SHIPPING FEVER IN STRESSED ANIMALS

CROSS REFERENCE OR DRAWINGS

Drawings none, reference U.S. Pat. No. 3,694,549.

SUMMARY

New uses for the Oak Poison Preventive.

BACKGROUND OF THE INVENTION

The formula used in the Oak Poison Preventative covered by U.S. Pat. No. 3,694,549 is: One part Citric acid, two parts ferrous sulfate, one part sodium bicarbonate, one half part succinic acid, and 7 parts of water. The citric acid is added to five parts of water, then the ferrous sulfate is added, this is allowed to stand ten minutes, and then the sodium bicarbonate is added. When the solution stops bubbling, the succinic acid, which has been added to two parts water is added to the solution. This is administered orally to the patient at the rate of one cc per two hundred pounds of body weight in any carrier that will deliver this dose to the patient daily. This dose may be increased or decreased as needed. Other intermediary metabolites may be substituted for succinic acid, but succinic acid is more stable and cheaper to use.

The Oak Poison Preventative has been used on race horses, at the rate of one cc per 200 pounds of body weight. It improves their hair coat, vitality, and racing performance. Oak Poison Preventative has been given to dogs experimentally at the rate of one drop per 10 (ten) pounds of body weight to increase vitality of old dogs. One of the things noticed is that a few drops of Oak Poison Preventative mixed in dog food increased the palatability of the dog food. This is a new use. Due to the increase in vitality in old dogs, I began taking the Oak Poison Preventative formula and it increased my vitality. Since I was taking the formula, a race horse trainer told his horse owner that I was taking the Oak Poison Preventative. The race horse owner began taking the Oak Poison Preventative supplement which his trainer was using on his horses. The trainer's wife called me, and asked? "Does the supplement reduce cholesterol in humans?" I told her, "I do not know." Then she told me their horse owner had been taking the supplement. He had his blood cholesterol level checked. His blood cholesterol level and his blood sugar were low, essentially normal. He is a border line diabetic. He stopped taking the supplement. He had his blood cholesterol level and blood sugar levels checked, they were very high. He started using the race horse supplement again, and his blood cholesterol levels and blood sugar levels returned to normal. Because of this I had my blood cholesterol level checked, since I had been taking the Oak Poison Preventative supplement for over ten years. My blood cholesterol level was a low 158 in spite of eating a high cholesterol diet. This is a valuable new discovery, of the properties of the Oak Poison Preventative supplement.

I am a practicing veterinarian, and one of my clients had four chronically ill cats. The cats were checked for leukemia on a blood test, and they were positive, for leukemia. The owner wanted them euthanized. When asked if we could experiment with one of the cats for a few days at no cost to the owner, the owner consented to the experiment. The first cat was given one half cc orally of the Oak Poison Preventative supplement. The cat improved and after 5 days of treatment, was sent home. Four cats were treated the same way and they all improved. Three of the cats were checked, two years later, and they were negative for the leukemia virus. The Oak Poison Preventive caused immuno-stimulation in the cats.

The Oak Poison Preventive has been used by people who fight chickens, and it improved the chickens fighting performance and appearance of their feathers.

The Oak Poison Preventive has been administered to feeder lambs and feeding the Oak Poison Preventive caused increased weight gains and a measureable increases in wool production, the increase in wool production, was not anticipated. (a new use)

When fed to stressed incoming feeder calves, to improve appetite, the feeding of Oak Poison Preventive to stressed calves, unexpectedly reduced the incidence of shipping fever in the calves, a new use.

DESCRIPTION AND ADVANTAGE OF THE INVENTION

I therefore, particularly point out and distinctly claim as new uses for the Oak Poison Preventative supplement.

I claim:

1. A method of using the Oak Poison Preventative to aid in the treatment of feline leukemia in cats comprising administering to said cats a therapeutically effective amount of the Oak Poison Preventative.

2. A method of using the Oak Poison Preventative to increase wool production in sheep comprising administering to said sheep a therapeutically effective amount of the Oak Poison Preventative.

3. A method of using the Oak Poison Preventative to aid in the treatment of shipping fever in cattle comprising administering to said cattle a therapeutically effective amount of the Oak Poison Preventative.

* * * * *